(12) United States Patent
Hauer

(10) Patent No.: US 10,154,617 B2
(45) Date of Patent: Dec. 11, 2018

(54) INTEGRAL METALLIC JOINT BASED ON ELECTRODEPOSITION

(71) Applicant: BIOTRONIK SE & Co. KG, Berlin (DE)

(72) Inventor: Marc Hauer, Uster (CH)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/613,470

(22) Filed: Jun. 5, 2017

(65) Prior Publication Data

US 2017/0359924 A1 Dec. 14, 2017

(30) Foreign Application Priority Data

Jun. 8, 2016 (DE) .................. 10 2016 110 539

(51) Int. Cl.
*H05K 5/06* (2006.01)
*H05K 9/00* (2006.01)
(Continued)

(52) U.S. Cl.
CPC ....... *H05K 9/0009* (2013.01); *A61M 5/14276* (2013.01); *A61N 1/0541* (2013.01); *A61N 1/362* (2013.01); *A61N 1/375* (2013.01); *A61N 1/39* (2013.01); *B81B 7/0058* (2013.01); *B81B 7/0064* (2013.01); *H01L 21/50* (2013.01);
(Continued)

(58) Field of Classification Search
CPC ............ H05K 5/00; H05K 5/02; H05K 5/062; H05K 5/069; H05K 9/009; H05K 5/066; H05K 5/065; H05K 5/06; A61M 5/14276; A61N 1/0541; A61N 1/362; A61N 1/39; A61N 1/05; A61N 1/375; A61N 1/37512; H01L 23/10; H01L 21/50; H01L 2224/16225; H01L 2924/16152
USPC ....... 174/50, 50.5, 50.52, 50.54, 50.61, 520, 174/539; 257/678, 684, 685, 686, 687, 257/699, 723, 731
See application file for complete search history.

(56) References Cited

U.S. PATENT DOCUMENTS

| | | | | |
|---|---|---|---|---|
| 4,372,037 A | * | 2/1983 | Scapple | H05K 5/0095 174/561 |
| 4,517,738 A | * | 5/1985 | Fukuoka | H01L 23/057 257/783 |

(Continued)

FOREIGN PATENT DOCUMENTS

| | | |
|---|---|---|
| DE | 10 2005 053765 A1 | 5/2007 |
| DE | 10 2011 112 476 A1 | 3/2013 |

(Continued)

OTHER PUBLICATIONS

German Search Report for German Case No. DE 10 2016 110 539.2, dated Dec. 14, 2016 (8 pages).

(Continued)

*Primary Examiner* — Angel R Estrada
(74) *Attorney, Agent, or Firm* — Buchanan Ingersoll & Rooney PC

(57) ABSTRACT

An electronic assembly, including an encasement joined from at least two casing parts, wherein at least one gap region between two mutually adjoining casing parts is hermetically sealed by a metal layer that is electrodeposited onto the sections of the adjoining casing parts abutting the gap region and bridges the gap region.

13 Claims, 4 Drawing Sheets

(51) Int. Cl.
*A61M 5/142* (2006.01)
*A61N 1/05* (2006.01)
*A61N 1/362* (2006.01)
*A61N 1/39* (2006.01)
*A61N 1/375* (2006.01)
*B81B 7/00* (2006.01)
*H01L 23/10* (2006.01)
*H01L 21/50* (2006.01)

(52) U.S. Cl.
CPC .......... *H01L 23/10* (2013.01); *H05K 5/062* (2013.01); *H05K 5/069* (2013.01); *A61N 1/37512* (2017.08); *H01L 2224/16225* (2013.01); *H01L 2924/16152* (2013.01)

(56) References Cited

U.S. PATENT DOCUMENTS

| | | | |
|---|---|---|---|
| 5,333,095 A | | 7/1994 | Stevenson et al. |
| 5,736,607 A | * | 4/1998 | Martin .................... H01L 23/10 |
| | | | 257/E21.505 |
| 5,750,926 A | * | 5/1998 | Schulman ............ H05K 5/0095 |
| | | | 174/564 |
| 8,946,879 B2 | * | 2/2015 | Goida ................. H01L 23/5389 |
| | | | 257/686 |
| 2002/0019669 A1 | | 2/2002 | Berrang et al. |
| 2009/0289349 A1 | | 11/2009 | Novotny et al. |

FOREIGN PATENT DOCUMENTS

| | | |
|---|---|---|
| DE | 101 64 494 B4 | 6/2014 |
| WO | 2001043517 A1 | 6/2001 |

OTHER PUBLICATIONS

European Search Report and Annex to the European Search Report on European Patent Application No. EP 17 17 4198.6, dated Nov. 11, 2017 (8 pages).

* cited by examiner

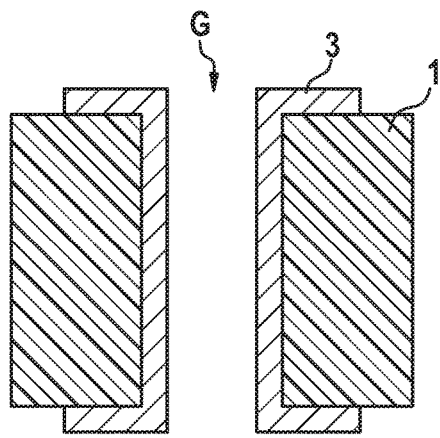
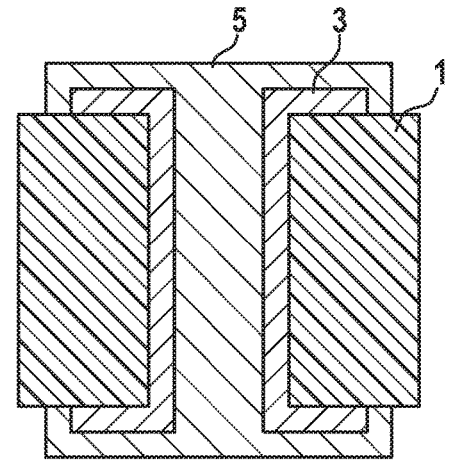
FIG. 1A  FIG. 1B
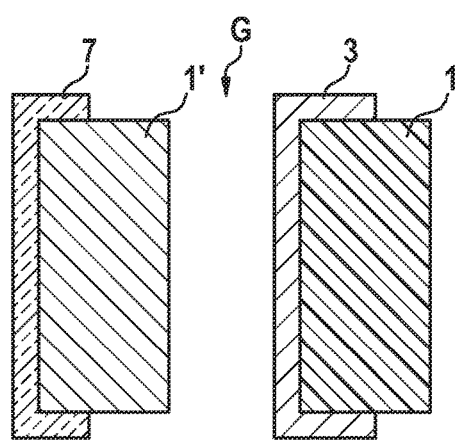
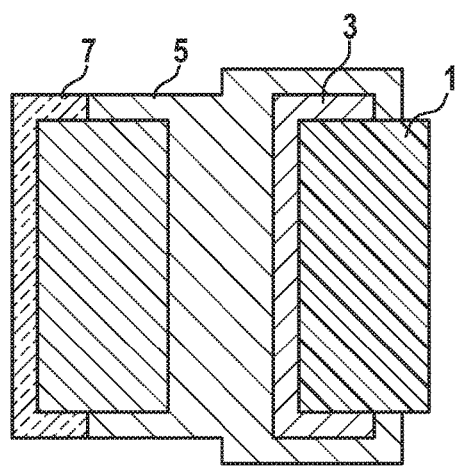
FIG. 2A  FIG. 2B

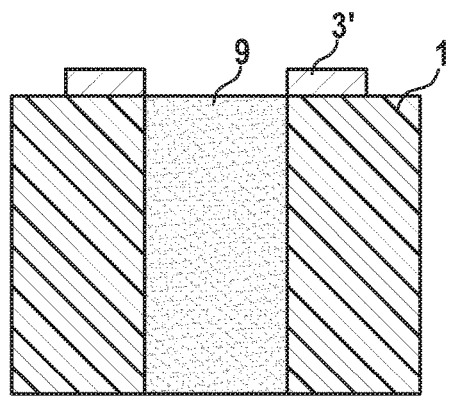
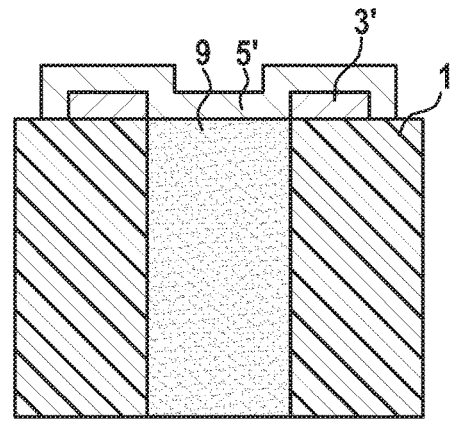
FIG. 3A  FIG. 3B
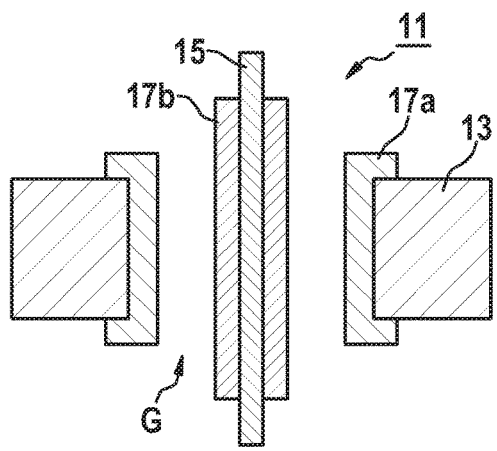
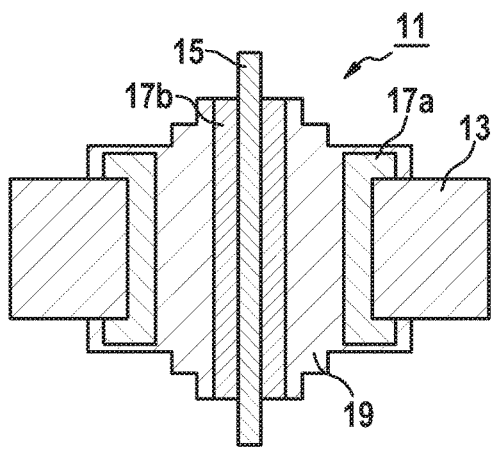
FIG. 4A  FIG. 4B

INTEGRAL METALLIC JOINT BASED ON ELECTRODEPOSITION

CROSS-REFERENCE TO RELATED APPLICATIONS

This patent application claims the benefit of and priority to co-pending German Patent Application No. DE 10 2016 110 539.2, filed on Jun. 8, 2016 in the German Patent Office, which is hereby incorporated by reference in its entirety.

TECHNICAL FIELD

The present invention relates to an electronic assembly, comprising an encasement joined from at least two casing parts, and, for example, also to an implantable electronic medical device. The present invention furthermore relates to a method for producing such an electronic assembly.

BACKGROUND

In certain application situations, it is necessary for electronic devices or assemblies to be completely ("hermetically") sealed. These include devices that must operate reliably under aggressive environmental conditions or in a living body on a permanent basis, which is to say, among other things, implantable electronic medical devices. However, on occasion, such hermetic sealing is also required for special assemblies in larger devices or equipment.

Proven methods exist for producing such sealed electronic assemblies or devices with reasonable complexity. Depending on the material and geometric configuration of the device encasement, these include welding methods (and in particular laser welding methods), soldering methods (and in particular brazing methods), sintering methods, and the like. In all these methods, the assembly or the device is subjected, at least in sections, to a relatively high thermal load, which results in corresponding thermal stresses and, possibly, also in a certain degree of damage to the materials used. In principle, these thermal stresses are not desired, or this certain degree of damage is not desired, but generally tolerated. A basic disadvantage of these methods is that the inevitable thermal load limits the spectrum of usable materials from the outset.

The present invention is directed toward overcoming one or more of the above-mentioned problems.

SUMMARY

It is therefore an object of the present invention to provide an electronic assembly that is improved in this regard, and a method for producing the same, wherein, in particular, thermal loads are to be substantially avoided during the production of the casing, along with the attendant limitations in the material selection.

At least this object is achieved in terms of the device aspect by an electronic assembly having the features of claim 1, and in terms of the method aspect by a method having the features of claim 11. Advantageous refinements of the inventive concept are the subject matter of the respective dependent claims.

The present invention encompasses the idea of sealing gaps between casing parts of the assembly or of the device in a "cold" process and thereby in an integral manner. In light of the known problems of permanently maintaining a hermetic seal at the interfaces of mutually joined parts, it furthermore includes the concept of providing a bridge or cover of the gap region, enclosing the abutting casing part surfaces. Additionally, the present invention covers the concept of providing this bridge or cover by way of a metal layer electrodeposited at least onto the sections of the adjoining casing parts which abut the gap.

An essential advantage of the proposed solution is the complete elimination of any thermal load whatsoever, and thus also the disadvantages associated therewith, and in particular thermal stresses and a limitation in the material selection. It shall be specifically pointed out in this regard that, according to the proposed concept, it is also possible to use materials having drastically differing coefficients of thermal expansion, and materials having very load thermal load capacity, for creating the assembly casing. Depending on the application, there may be other advantages, such as, for example, the elimination of a thermal load of the components or parts received in the assembly casing, a reduction in the energy expenditure during production, and thus also in the production costs, and the like.

In one practically important embodiment, the assembly is designed as an implantable electronic medical device, and in particular as a cardiac pacemaker, a cardioverter, a cochlear implant, or a drug dosing pump. Hermetic sealing is a fundamental requirement for such devices, and the conventional thermal processes, for example, for forming the so-called feedthrough between the housing main part and the header of a pacemaker or cardioverter, but also in part for forming the housing main part, previously resulted in significant limitations in the material selection. Implementations of the proposed assembly in the form of a completely hermetically sealed device, however, are not limited to implantable or, in more general terms, to electronic medical devices, but such devices can also be important in the process control of exploration or chemical plants, in aircraft engineering, in the aerospace industry, and the like.

In one further embodiment, the electronic assembly is designed as a hermetically sealed and, optionally, an EMI-tight component of an electronic device that is not sealed in the overall. In particular, this can involve regions of an assembled printed circuit board or of another circuit substrate provided with a top or a cover, which is subject to higher requirements in terms of the tightness than other regions or assemblies of the corresponding device.

In a further embodiment, at least one of the adjoining casing parts is a metal part having an uncoated surface beneath the deposited metal layer. The corresponding metal part can also be one that, per se, does not tend to form a natural oxide layer (which would prevent the electrodeposition), which is to say in particular gold or another noble metal. However, this part may also have been subjected to a cleaning process immediately prior to the electrodeposition and/or have been joined or coated in advance with a non-corroding metal.

In a further embodiment, at least one of the adjoining casing parts is a plastic part, and in particular a printed circuit board, or a ceramic part, and in particular a thick-film substrate, comprising an additional metallization layer beneath the deposited metal layer. The additional metallization layer (which can also be implemented as an applied or attached additional metal part) ensures the necessary electrical conductivity for the subsequent metal deposition from the electrolyte. In principle, it is only required in the region or along an edge where the sealing metal layer is, in fact, to be formed.

In a further embodiment of the present invention, the mutually adjoining casing parts are joined by way of an adhesive, which substantially fills the gap region and is conductive at least on the outer side thereof. It is sufficient, in principle, if the adhesive on the outer surface of the gap is conductive, or was rendered conductive, such as, for example, by way of a superficially introduced metal powder or the like. Typically, however, a homogeneous conductive adhesive will be used since, technologically, this is easier. Depending on the application, it is possible to dispense with rendering an electrically insulating casing part conductive in advance when an adhesive joint is used that was at least superficially rendered conductive. This would, in particular, be possible if conductive adhesive is also applied to the surface section of the insulating casing part which abuts the gap, thus "metallizing" the same so-to-speak.

In further embodiments of the present invention, it is provided that the electrodeposited metal layer forms a tight, pore-free layer and thereby suppresses diffusion. Depending on the requirements profile, this can involve inert metals, such as, for example, gold, platinum or palladium, or non-inert metals, such as, for example, Cu or No. In a special embodiment, the deposition can also comprise multiple metals in the form of an alloy or layer sequence. Typical metal layer thicknesses range between 0.1 and 100 µm.

In the above-described embodiment as an electronic medical device, the electrodeposited metal layer can, in particular, be provided on a feedthrough of the electronic medical device and, in particular, can bridge and seal the gap region between the flange part and a conductor element of the feedthrough. Specifically, it may be provided that the flange part is made of titanium and partially provided with a noble metal additional part or a noble metal layer, and the conductor element comprises a plastic or ceramic substrate and is partially provided with a noble metal layer.

Furthermore, it is also possible in the case of such an implantable device for the actual housing to be composed according to the present invention, which is to say, in particular, of two housing shells, for the gap region to be covered, and thus hermetically sealed, by an electrodeposited metal layer.

In the implementation as an individual assembly of a larger device, as was likewise described at the outset, one of the adjoining parts can be a printed circuit board or a thick-film substrate, and the other part can be a metallic cover part, and the printed circuit board or the thick-film substrate can comprise a partial metal coating, which is configured in keeping with the opening contour of the cover part and serves as a base for the electrodeposited metal layer.

Method aspects of the present invention in preferred embodiments are derived partially from the device aspects described at the outset and thus do not need to be repeated here. In principle, the essential steps of the proposed method can be described as follows:

providing two casing parts that are inherently suitable or prepared for electrodeposition;

arranging the casing parts in a predetermined relative position with respect to one another, which encloses a gap region therebetween, and fixing the relative position of the casing parts;

placing the casing parts fixed in the relative position thereof in an electrolysis bath; and carrying out an electrodeposition process in the electrolysis bath under method conditions that ensure the deposition of a metal layer bridging and hermetically sealing the gap region.

It shall be mentioned that the casing parts for the electrodeposition advantageously are positioned as close as possible to one another, which is to say with a preferably small gap region. However, during mass production, dimensional tolerances of the casing parts must, of course, be observed, and a readjustment of the position for each individual assembly or each individual device will normally not be expedient with regard to the costs. With respect to the method conditions to be set, it should be mentioned that the deposited metal layer must be sufficiently thick so as to ensure permanent hermetic sealing in the gap region, and, depending on the application, also in the case of certain mechanical stresses of the assembly casing or device casing and/or in the case of alternating temperature stress loads during operation.

In embodiments of the present invention, the electrodeposition is carried out in an electrolysis bath, which has a dense layer structure and good adhesion. Preferably, electrolytes may be used which allow an accelerated deposition in a gap compared to the surface (such as, for example, Dow Chemical EVF).

In a further embodiment, the electrodeposited metal layer comprises multiple metals in the form of an alloy and/or a layer sequence comprising different metals in each sublayer.

In still another embodiment, the electrodeposited metal layer has a thickness in the range between 0.1 and 100 µm.

Further embodiments, objectives, features, advantages and possible applications of the present invention will become clear from the following description of exemplary embodiments with reference to the drawings. Here, all features described and/or illustrated in the drawings form the subject matter of the present invention, independently or in any combination, even regardless of their summary in the claims and the dependency references of the claims.

DESCRIPTION OF THE DRAWINGS

Advantages and functional characteristics of the present invention will additionally become apparent hereafter from the description of exemplary embodiments based on the figures. In the drawings:

FIGS. 1A and 1B show schematic diagrams to explain a basic embodiment of the present invention;

FIGS. 2A and 2B show schematic diagrams to explain a further basic embodiment of the present invention;

FIGS. 3A and 3B show schematic diagrams to explain a further basic embodiment of the present invention;

FIGS. 4A and 4B show schematic diagrams to explain one embodiment of the present invention in an implantable electronic medical device;

DETAILED DESCRIPTION

Figure 5A:
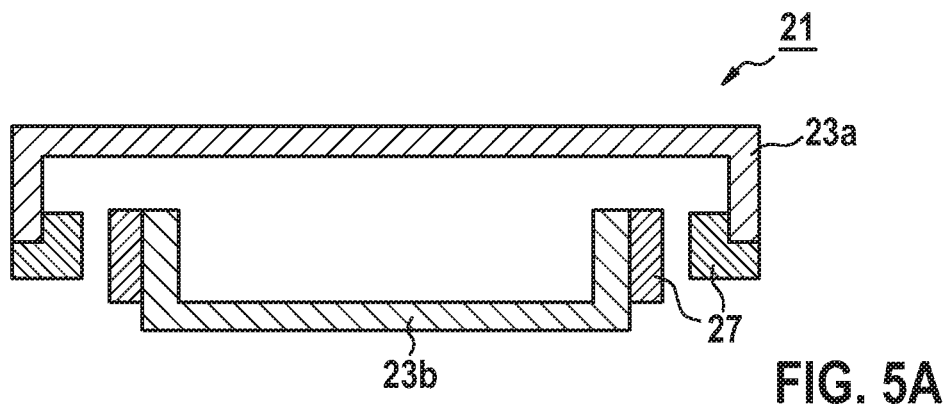
FIGS. 5A to 5C schematic diagrams to explain a further embodiment of the present invention in an implantable electronic medical device.

FIG. 1A, schematically in the manner of a longitudinal section, shows two workpieces (casing parts of a device casing) 1, which are to be joined to one another in a hermetically sealed manner at the mutually facing surfaces thereof by way of the method according to the present invention, and FIG. 1B shows the workpieces (casing parts) in the sealed and joined final state. So as to be able to apply the inventive method, the casing parts 1 were each partially provided with a conductive coating 3, and more particularly across the full surface areas on the mutually facing surfaces, and additionally in a portion of the upper and lower faces thereof. They are then fixed relative to one another, keeping a predetermined gap G therebetween, and introduced into an electrolysis bath, where a metal layer 5 is electrodeposited (grown) onto all metallic surfaces and thereby closes the gap G completely and in a hermetically sealed manner.

FIG. 2A, in turn, shows two pretreated casing parts 1, 1', however comprising a different material configuration. The casing part 1 is again produced from an insulating material (such as, for example, plastic or ceramic), while the casing part 1' is a metal part. As with the above-mentioned embodiment, so as to make it possible to carry out the method, the non-conducting part 1 is partially provided with a metal coating 3, while the metallic part is provided with an insulating layer 7 on a portion of the surfaces thereof to prevent the same from being completely covered by an electrodeposited metal layer. Again, the parts are brought into a fixed position relative to one another and treated under predetermined process conditions in an electrolysis bath, whereby the configuration shown in FIG. 2B is formed. As with the first embodiment, all metallic surfaces are covered by a deposited metal layer here, which also forms the original gap between the casing parts 1, 1' and provides a hermetically sealed joining site.

FIGS. 3A and 3B show a further embodiment in which two non-conducting parts 1 are joined to one another at one of the mutually facing surfaces across the full surface area by way of a conductive adhesive 9 after the upper faces thereof were partially provided with a local metal layer (or with a pressed-on small metal part) 3'. The parts are only partially immersed into an electrolysis bath here since only the upper faces thereof (including the free upper face of the adhesive layer 9) are to be provided with a deposited metal layer, and the upper face metallization 5' forms during the electrodeposition process. This upper face metallization provides, in particular, a diffusion barrier on the adhesive layer 9 and hermetically seals the integral joint that already existed beforehand. In this configuration, the amount of metal consumed for the pretreatment and the electrodeposition is also considerably lower, and the electroplating process can be completed more quickly. Furthermore, this simplifies the orientation of the parts with respect to one another during the electrodeposition.

While the above exemplary embodiments are of a very general nature and, in terms of the application thereof, are not limited to casing parts of an electronic assembly or certain devices, FIGS. 4A and 4B show a more specific configuration, which is to say that of a feedthrough 11 of an implantable electromedical device (not shown). Here, a titanium flange 13 and a printed circuit board 15, which is based on a liquid crystal polymer (LCP) material and penetrates the flange 13 perpendicularly to the extension plane thereof, are to be joined to one another in a hermetically sealed manner.

Analogously to the above-described first and second embodiments, both the surface of the titanium flange 13 and that of the LCP printed circuit board 15 are partially metallized, and more particularly by way of an attached gold ring 17a or a gold coating 17b. This pretreatment is also necessary in the case of the titanium flange 13 since the surface thereof carries a natural corrosion layer, which would prevent electrodeposition. In the final state shown in FIG. 4B, a deposition metallization 19 is formed, which joins the titanium flange 13 and the LCP printed circuit board 15 to one another, fills the annular gap G therebetween and hermetically seals the components with respect to one another. Again, a modification here is to join the components beforehand in an integrally bonded manner using a conductive adhesive, which, in particular, reduces the amount of gold that would otherwise be needed to render the mutually facing surfaces conductive and, additionally, simplifies the positioning of the components during the electrodeposition.

Figure 5B:
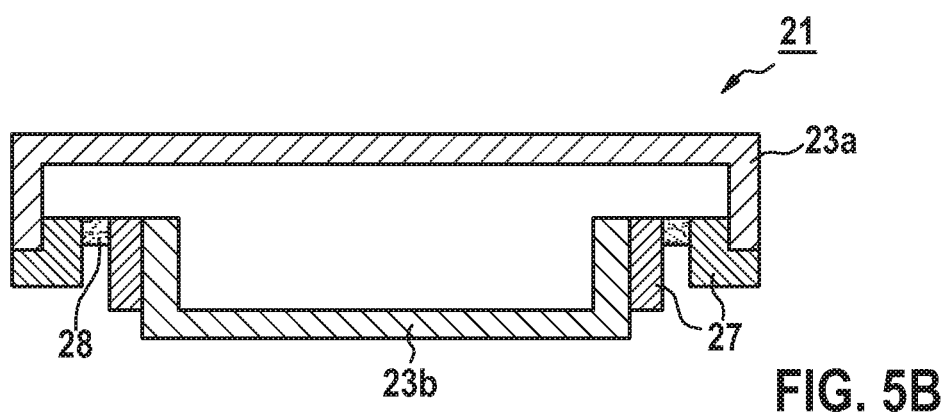
Figure 5C:
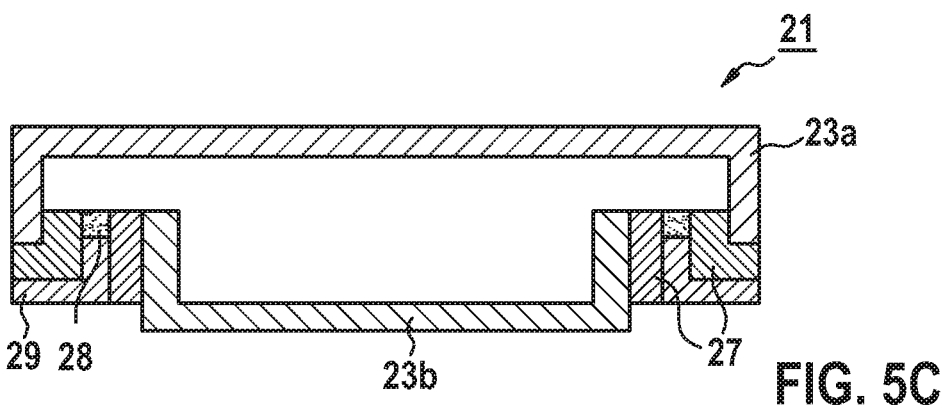

FIGS. 5A to 5C schematically shows a further embodiment of the present invention in the manner of a longitudinal section, in which two titanium half shells 23a, 23b of an implant housing 21 are assembled and sealed. Beforehand, the edges of the half shells 23a, 23b are provided with a gold coating 27. Thereafter, a line of conductive adhesive 28 is introduced in the remaining gap between the edges of the half shells 23a, 23b, which have been fixed in the relative position thereof, and is cured. In the electrolysis bath, an electrodeposited metal layer 29 then forms on the surfaces of the partial gold layer and the free surface of the conductive adhesive, this metal layer hermetically sealing the implant 23. According to the present invention, sealing takes place without the implant being exposed to elevated temperatures, which cannot be avoided with the typically employed laser welding process.

Figure 6A:
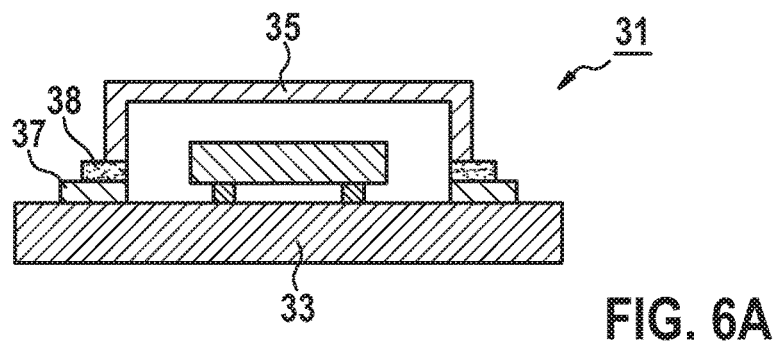
FIGS. 6A and 6B show schematic diagrams to explain one embodiment of the present invention in a delimited electronic assembly of a device.
Figure 6B:
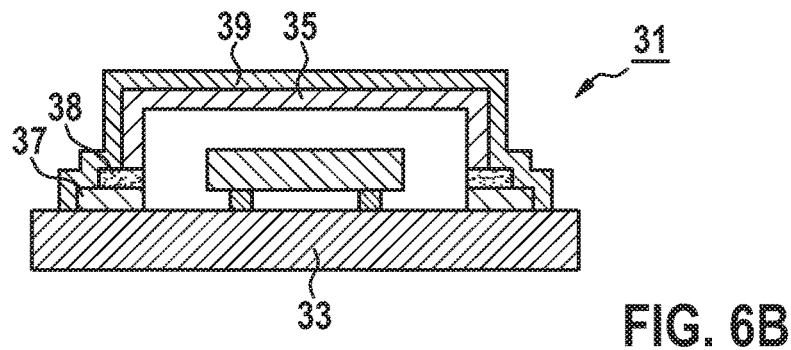

FIGS. 6A and 6B, again in schematic longitudinal sectional illustrations, show a section of a circuit substrate 33 of an electronic assembly 31 which is provided with a protective cover 35. While the cover 35 is made of a metal having an uncoated surface, which can be electroplated without pretreatment, prior metallization 37 is again required on the circuit substrate (such as, for example, a printed circuit board based on plastic material or a ceramic substrate) in the edge region of the cover to be attached. Alternatively, this metallization can be formed of the same material as the printed conductor tracks on the substrate and can be generated simultaneously with the conductive pattern. An adhesive bead 38 made of a conductive adhesive is applied to this metallization 37, and the cover 35 is attached thereto, so that initially bonding between the cover and the circuit substrate takes place. Subsequently, galvanic metallization takes place, which provides the covering and hermetically sealed metal coating 39.

If the circuit substrate itself is hermetically sealed (as is the case with ceramic material, for example) or is substantially hermetically sealed (for example, in the case of an LCP-based printed circuit board), diffusion from the surroundings into the interior of the sealed assembly is no longer possible, or almost not possible. In conjunction with the metallization coating the cover and the adhesive bead, a biocompatible, hermetic package can be produced, without necessitating the use of thermal processes exceeding 100° C.

Figure 7A:
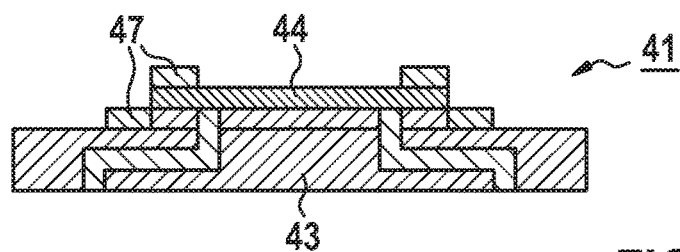
FIGS. 7A and 7B show schematic diagrams to explain a further embodiment of the present invention in a delimited electronic assembly of a device.
Figure 7B:
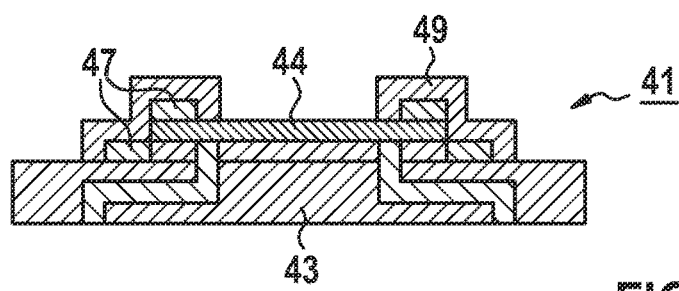

FIGS. 7A and 7B show a modification of the embodiment described last of an assembly 41, which, again, is based on a ceramic or plastic substrate 43. The main functional component is a sensor element 44 here, comprising appropriate connections (not shown separately here) extending through the circuit substrate 43. Here, hermetic sealing of the peripheral edge of the sensor element 44 on the substrate 43 is required. For this purpose, a metallization 47 capable of electroplating is applied both to the peripheral edge of the sensor element and to the adjoining regions of the substrate 43. The surface regions of the sensor 44 and of the circuit substrate 43 which were not previously metallized cannot be electroplated due to the lack of conductivity thereof. After treatment in the electrolysis bath, the configuration shown in FIG. 7B is obtained, comprising a metal layer 49 that partially covers the sensor element in an annular manner and is peripherally deposited. This establishes a hermetically sealed joint between the sensor element and the circuit substrate in the edge region of the sensor element.

The implementation of the invention is not limited to the examples and aspects described above, but is likewise possible in a plurality of modifications, which are within the capabilities of those skilled in the art. It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. An electronic assembly, comprising:
    an encasement joined from at least two casing parts, wherein at least one gap region between two mutually adjoining casing parts is hermetically sealed by a metal layer that is electrodeposited onto sections of the adjoining casing parts abutting the gap region and bridges the gap region,
    wherein the mutually adjoining casing parts are joined by way of an adhesive, which substantially fills the gap region and is homogenously conductive.

2. The electronic assembly according to claim 1, designed as an implantable electronic medical device, including as a cardiac pacemaker, a cardioverter, a cochlear implant, or a drug dosing pump.

3. The electronic assembly according to claim 1, designed as a hermetically sealed EMI-tight component of an electronic device that is not sealed in the overall.

4. The electronic assembly according to claim 1, wherein at least one of the adjoining casing parts is a metal part comprising an uncoated surface beneath the deposited metal layer.

5. The electronic assembly according to claim 1, wherein at least one of the adjoining casing parts is a non-conducting part, including a plastic part comprising a printed circuit board, or a ceramic part comprising a thick-film substrate, comprising an additional metallization layer beneath the deposited metal layer.

6. The electronic assembly according to claim 1, wherein the electrodeposited metal layer forms a tight, pore-free layer and comprises an inert metal including gold, platinum or palladium, or a non-inert metal including Cu or Ni.

7. The electronic assembly according to claim 2, wherein the electrodeposited metal layer is provided on a feedthrough of the electronic medical device and bridges and seals the gap region between a flange part and a conductor element of the feedthrough.

8. The electronic assembly according to claim 3, wherein one of the adjoining parts is a printed circuit board or a thick-film substrate, and the other part is a metallic cover, and the printed circuit board or the thick-film substrate comprises a partial metal coating, which is configured in keeping with the opening contour of the cover part and serves as a base for the electrodeposited metal layer.

9. The electronic assembly according to claim 1, wherein the electrodeposited metal layer comprises multiple metals in the form of an alloy and/or a layer sequence comprising different metals in each sub-layer.

10. The electronic assembly according to claim 1, wherein the electrodeposited metal layer has a thickness in the range between 0.1 and 100 μm.

11. A method for producing an electronic assembly according to claim 1, comprising the following steps:
    providing two casing parts that are inherently suitable or prepared for electrodeposition;
    arranging the casing parts in a predetermined relative position with respect to one another, which encloses a gap region therebetween, and fixing the relative position of the casing parts;
    placing the casing parts fixed in the relative position thereof in an electrolysis bath; and
    carrying out an electrodeposition process in the electrolysis bath under method conditions that ensure the deposition of a metal layer bridging and hermetically sealing the gap region,
    wherein fixing of the relative position of the casing parts comprises the bonding thereof by way of a conductive adhesive, which substantially fills the gap region and is homogenously conductive, and at least partially curing the adhesive.

12. The method according to claim 11, wherein the provision of the casing parts prepared for electrodeposition comprises the at least partial application of a metallization or the joining to a noble metal part of at least one of the casting parts.

13. An electronic assembly, comprising:
    an encasement joined from at least two casing parts, wherein at least one gap region between two mutually adjoining casing parts is hermetically sealed by a metal layer that is electrodeposited onto sections of the adjoining casing parts abutting the gap region and bridges the gap region,
    wherein the electronic assembly is designed as an implantable electronic medical device, including as a cardiac pacemaker, a cardioverter, a cochlear implant, or a drug dosing pump,
    wherein the electrodeposited metal layer is provided on a feedthrough of the electronic medical device and bridges and seals the gap region between a flange part and a conductor element of the feedthrough, and
    wherein the flange part is made of titanium and partially provided with a noble metal additional part or a noble metal layer, and the conductor element comprises a plastic or ceramic substrate and is partially provided with a noble metal layer.

* * * * *